United States Patent
Kaltwasser et al.

(10) Patent No.: US 6,372,715 B1
(45) Date of Patent: Apr. 16, 2002

(54) USE OF ERYTHROPOIENTIN AND IRON PREPARATIONS FOR PRODUCING PHARMACEUTICAL COMBINATION PREPARATIONS FOR TREATING RHEUMATIC DISEASES

(75) Inventors: Joachim Peter Kaltwasser, Frankfurt am Main; Paul Lehmann, Worms, both of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/485,371

(22) PCT Filed: Aug. 5, 1998

(86) PCT No.: PCT/EP98/04864

§ 371 Date: Feb. 8, 2000

§ 102(e) Date: Feb. 8, 2000

(87) PCT Pub. No.: WO99/07401

PCT Pub. Date: Feb. 18, 1999

(30) Foreign Application Priority Data

Aug. 8, 1997 (DE) .......................................... 197 34 293

(51) Int. Cl.⁷ ........................ A61K 38/00; G01N 33/564
(52) U.S. Cl. ............................. 514/2; 436/509; 514/12; 514/825
(58) Field of Search .......................... 436/509; 514/825, 514/2, 12

(56) References Cited

FOREIGN PATENT DOCUMENTS

| EP | 0 025 721 | 3/1981 |
| GB | 2 171 304 | 8/1986 |
| WO | WO 96/14081 | 5/1996 |
| WO | WO 97/09996 | 3/1997 |

OTHER PUBLICATIONS

Pincus et al. Multicenter Study of Recombinant Human Erythropoietin in Correction of Anemia in Rheumatoid Arthritis. (1990) Am. J. Med. vol. 89, pp. 161–168.*

Nordstrom et al., Rheumatology International, 1997, 17 (2), pp. 67–73.

Hochli et al., European J. Haematology, 1993, 51(1), pp. 54–55.

* cited by examiner

Primary Examiner—Christopher S. F. Low
Assistant Examiner—Holly Schnizer
(74) Attorney, Agent, or Firm—George W. Johnston; Dennis P. Tramaloni

(57) ABSTRACT

The present invention is concerned with the use of individual administration forms of an erythropoietin preparation and a physiologically compatible iron preparation corresponding to an equivalent amount of 1–40 mg of iron ions for the production of a pharmaceutical combination preparation for the treatment of rheumatic diseases.

11 Claims, 2 Drawing Sheets

USE OF ERYTHROPOIENTIN AND IRON PREPARATIONS FOR PRODUCING PHARMACEUTICAL COMBINATION PREPARATIONS FOR TREATING RHEUMATIC DISEASES

BACKGROUND OF THE INVENTION

The present invention is concerned with the use of erythropoietin and iron preparations for the production of pharmaceutical combination preparations. These combination preparations comprise individual administration forms of an erythropoietin preparation and a physiologically compatible iron preparation corresponding to an equivalent amount of 1–40 mg of iron ions for the treatment of rheumatic diseases.

Pharmaceutical combination preparations containing erythropoietin and iron preparations are known from PCT Patent Application WO 97/09996. The preparations are utilized especially for the optimization of erythropoiesis in the treatment of illnesses in which a stimulation of erythrocyte formation is striven for.

The use of erythropoietin for the treatment of chronic inflammations, especially of rheumatoid arthritis, is known from WO 96114081.

The therapeutic treatment of patients suffering from rheumatic diseases has hitherto still not been possible using a satisfactory treatment regimen. In this respect, there exists a need for improved treatment methods, such as, for example, in the treatment of rheumatoid arthritis, lupus erythematosus, Bechterew's disease, etc.

Rheumatic diseases of the locomotor system and inflammatory joint diseases are worldwide one of the main causes of chronic pains and severe bodily damage. All elements of the musculoskeletal system are in a dynamic equilibrium and their form, structure and functional state change constantly depending on loading and mechanical requirements. This system is susceptible to trauma and responsive to localized and systemic inflammatory disorders. Acute inflammatory conditions or tissue injuries often result in chronic conditions, possibly because of the constant movements and mechanical loadings.

Joint diseases belong to diseases of the locomotor system and are sub-divided into those which concern the periarticular tissue and those which are true joint diseases (e.g. arthrosis). Symptoms and diagnoses can often lead back to a systemic, generalized disease or also to illnesses which primarily emanate from another system or organ.

Immune-mediated inflammation plays an important role in the pathological course of rheumatic disorders. In many cases immune-mediated inflammation is the basis of numerous systemic connective tissue diseases. Infectious processes are also of significance, primarily in diseases such as rheumatic fever, Lyme borreliosis or reactive arthritis. The etiology of rheumatic diseases may be multi-factorial, with genetic reasons and environmental effects also having an important influence.

Pain is a major symptom of most rheumatic diseases, especially of joint diseases. Hitherto, the causes of joint pain have been largely unclear. A therapeutic control of joint pain is possible at present only in an inadequate manner. Also, the decisive factors of a loss of function have previously not been completely clear. Many of the most important joint diseases show in their incidence remarkable differences between sexes; thus, SLE occurs primarily in women, while ankylosing spondylitis occurs more frequently and in more severe form in men. The reasons for this are likewise unclear.

The incidence, prominence and consequences of diseases of the locomotor system depend on age and sex. Some diseases occur only in childhood (juvenile chronic arthritis); others, such as SLE or ankylosing spondylitis, begin mainly in young adults, polymyalgia rheumatica and granulomatous arteritis on the other hand almost never occur before the age of 55. cP, SLE, gout and other serious inflammatory rheumatic diseases show a different initial prominence with increased age. Most of these diseases of the locomotor system cause chronic pain.

No medicament having a satisfactory activity is available for healing these chronic rheumatic diseases. The therapeutic principles used in the treatment are frequently based on and often depend on factors such as the age and overall situation of the patient and the extent of inflammatory activity and of the consequences (pain intensity, extent of impediment). The treatment plan used in practice for patients with severe diseases of the locomotor system is composed of different measures and is in this respect often dependent on the treating physician. A uniform and generally accepted treatment method has hitherto not been established.

SUMMARY OF THE INVENTION

It has surprisingly now been found that a positive influence on the overall disease picture in patients with rheumatic diseases and an improvement in the general health and the quality of life of these patients can be achieved with the aid of an optimal amount of EPO and iron in the form of a corresponding combination preparation. Further, an optimal activity of EPO and respectively, of the iron preparation employed is achieved. In particular, the costs of the treatment with EPO can be clearly reduced in that, for example, lower dosages of the active substance can be administered. The combination preparations in accordance with the invention are especially suitable for the treatment of inflammatory joint diseases. Further, in many patients a clear alleviation of pain can be achieved.

DETAILED DESCRIPTION OF THE INVENTION

Figure 1:
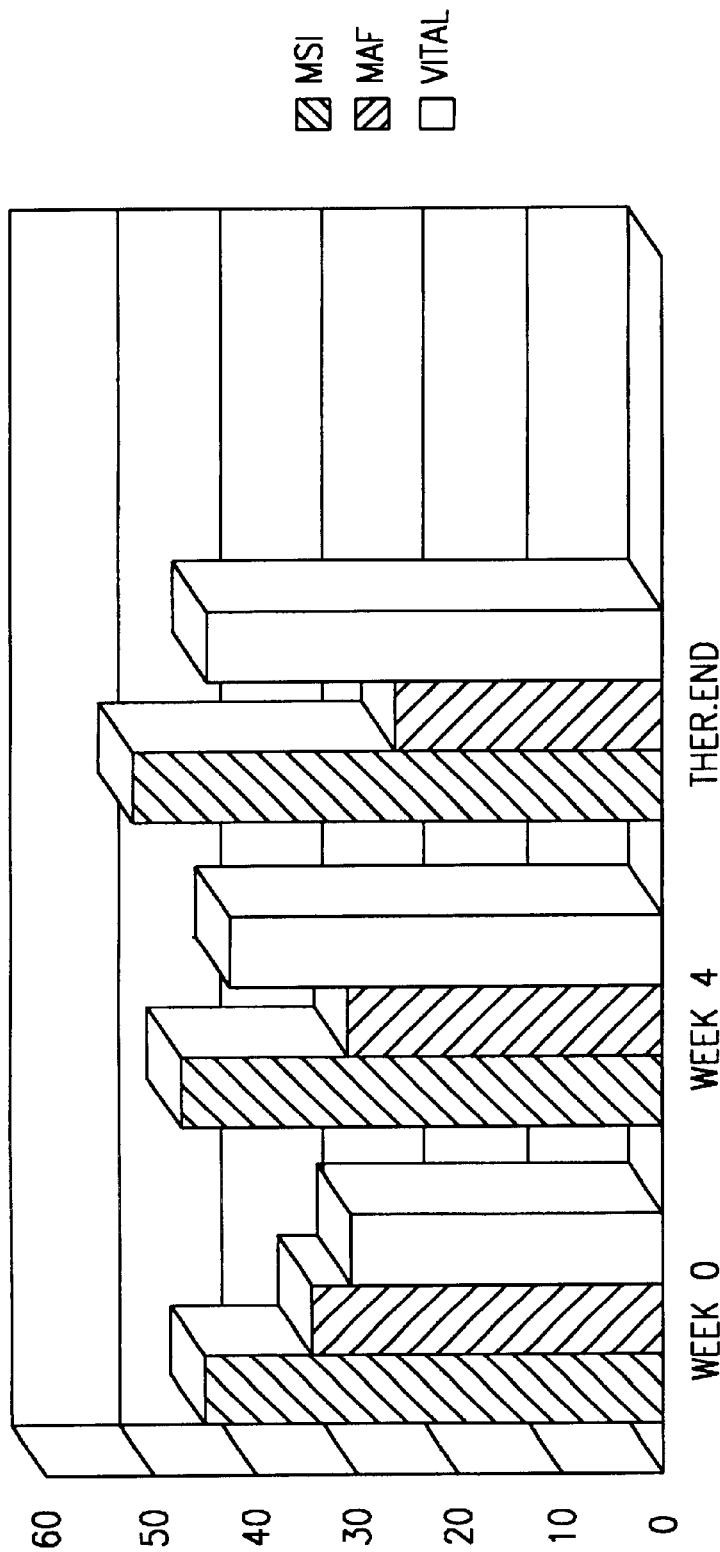
FIG. 1: Effects of treatment with EPO and iron sucrose according to Example 1. Isometric Muscle Strength (MSI) fatigue scale (MAF) and vitality scores are shown.

In the meaning of the present invention there are used especially those pharmaceutical combination preparations which contain 250–20,000 U of an erythropoietin preparation and 1–40 mg of an equivalent amount of iron ions of physiologically compatible iron preparation, whereby the erythropoietin preparation and the iron preparation can be present in separate administration form or in a single administration form. The combination preparations preferably contain 1–30 mg, particularly 3–20 mg, of an equivalent amount of iron ions of a physiologically compatible iron preparation, especially a Fe(II) or Fe(III) complex.

As suitable erythropoietin preparations in the meaning of the present invention there come into consideration those active substances which are comparable with respect to the physiological effect of human EPOs. Suitable EPO preparations are, for example, recombinant human EPO (rhEPO; see European Patent EP 0,205,564 or EP 0,411,678) or also corresponding modifications of these proteins. As modifications there come into consideration, for example, such proteins with molecular weights higher or lower than 34,000 Da (molecular weight of urinary EPO), likewise isoforms of the enzyme or proteins with different glycosylation. In particular, proteins chemically modified by PEG (polyethylene glycol) can also be used. Further, there basically also come into consideration such proteins which are derived by deletions, substitutions or additions of one or more amino acids of the amino acid sequence of the natural EPO with a length of 166 amino acids. These proteins have essentially comparable physiological properties to rhEPO. In particular, these proteins have biological properties which cause bone marrow cells to increase the production of reticulocytes and red blood corpuscles and/or to increase haemoglobin synthesis or iron uptake. In place of these proteins there can also be used low molecular substances, which are denoted as EPO mimetics, and which bind to the same biological receptor. These mimetics can preferably also be administered orally. The amount of such proteins or mimetics to be administered is determined by comparing the biological activity between EPO and these active substances.

Oral iron resorption is only about 1 mg per day and under extreme loading (in the case of oral administration of about 300 mg Fe(III)/day) less than 3 mg per day. Therefore, the intravenous administration of iron preparations is increasingly preferred. Two intravenously administerable iron preparations are available on the German medicament market at present. These are the medicaments "Ferrlecit" and "Ferrum Vites". "Ferrlecit" is an iron(III) gluconate complex, while "Ferrum Vites" is an iron(III) hydroxide saccharate complex.

The manifold problems of a high dosage, long-term oral iron therapy can be circumvented relatively simply by the intravenous, subcutaneous administration of physiologically compatible iron(III) salts during haemodialysis treatment, since in this case a safe intravenous, subcutaneous access exists and the injection can be effected without further burden on the patients. The intravenous administration of iron preparations is, however, not trivial, since with the administration of high doses side effects have to be taken into consideration, primarily when large amounts have to be injected relatively rapidly. Further, the intravenous administration of iron preparations causes problems up to acute phase reactions when the iron dose given is too high or is not optimally correlated with the EPO dose. Iron poisoning can also occur in the case of a too high dosage of iron-containing preparations. Elementary iron has a toxic effect on the gastrointestinal tract and on the cardiovascular and central nervous systems. The oral lethal dosage of elementary iron varies between 200 and 250 mg/kg. The most frequently used iron tablets are ferrous sulphate (contains about 20% elementary iron), ferrous fumarate (contains about 30% elementary iron) and ferrous gluconate (contains about 10% elementary iron).

Iron preparations in the meaning of the present invention are oral or parenteral administration forms. These can be basically individual preparations, which contain a physiologically compatible iron salt or an iron complex compound as the active substance, or also combination preparations, which in addition to the physiologically compatible iron preparation contain other active substances, such as e.g. vitamins, folic acid, thiamine chloride, riboflavin, pyridoxine, ascorbic acid, nicotinamide, calcium pantothenate, etc.

Physiologically compatible iron salts or iron complex compounds are, for example, iron(II) sulphate, iron(II) fumarate, iron(II) citrate, iron(II) gluconate, iron(II) succinate, iron(II) chloride, iron(II) glycine sulphate complex, iron(II) aspartate, sodium iron(III) gluconate complex, iron(III) hydroxide polymaltose complex or ferrisorbitol citrate complex. Preferred iron preparations are especially Fe(III) complexes, especially those with a molecular weight between 30,000 and 100,000 D. Fe(III) saccharate is especially preferred. Here, reference can be made to the commercially available preparation "Ferrum Vitis" (manufactured by Neopharma, Germany). By virtue of the low iron dosage in accordance with the invention it is also possible to utilize labile iron complexes, such as iron gluconate (mol. wt. about 1,000 D; Ferrlecit), in the combination preparation, although these labile iron complexes liberate relatively large amounts of ionized iron, which would lead to toxicities in the case of the intravenous administration of large amounts.

Hereinafter there is to be understood with respect to the amount of the iron preparation basically the equivalent amount of iron ions, Fe(II) or Fe(III) ions, to be administered. By this standardization the amount of an arbitrary iron preparation can be calculated on the basis of its known molecular weight. In the case of iron(III) gluconate×2 $H_2O$, for example, the amount of iron is 80.5 mg when an amount of 695 mg of the iron preparation is administered. When, for example, 280 mg of anhydrous iron(II) succinate are administered, the amount of iron is 95.2 mg.

In the meaning of the present invention there should be understood under the term "combination preparation" not only those medicament packs in which the EPO preparation and the iron preparation are presented in juxtaposition in a finished marketable unit pack (so-called combination pack), but also those medicament packs which either contain a suitable amount of an EPO preparation or a suitable amount of an iron preparation in the form of the respective individual preparations, with the individual preparations with respect to the amount of contents being presented such that they can be administered in the meaning of the invention for the combined dose with the respective other preparation. In these cases there is usually enclosed with the preparations from the pharmaceutical manufacturer or the medicament importer a medicament package insert which is required by law in many countries and in which are contained directions or information concerning the combined dose of the individual preparations. Preferably, the combination preparations can be present in a single administration form in which the respective amounts of the EPO preparation and the iron preparation are present in juxtaposition in one container.

For the treatment of haemodialysis patients, the combination preparation in accordance with the invention contains, for example, 250 to 15,000 U (the abbreviation "IU" for International Units can also be used in place of the abbreviation "U") of an EPO preparation, especially 500 to 10,000 U. Preferred dosages are 250 U, 500 U, 1,000 U, 2,000 U, 5,000 U, 7,500 U and 10,000 U per individual dose. The amount of iron ions is advantageously up to 30 mg, preferably 3–20 mg, especially 5–20 mg, and particularly about 10 mg. For the treatment of anaemia patients, the optimal dosage is 500 to 10,000 U, preferably about 1,000–3,000 U. In this case, the amount of iron ions is advantageously up to 30 mg, for example 3–15 mg and especially about 5 mg.

The concentrations in accordance with the invention of EPO and of the iron complex permit in their combination an optimal adjustment and treatment of patients suffering from rheumatic diseases and in the case of intravenous iron therapy do not lead to acute phase reactions.

The treatment with the combination preparation is effected once to five times weekly, preferably up to four times weekly, with the total amount of iron per patient not exceeding 100 mg per week. In the treatment of patients with rheumatic diseases, a total amount of 80 mg, especially 50 mg, of iron ions per week should advantageously not be exceeded. A particular advantage of the combination preparation in accordance with the invention in clinical practice lies in the fact that it can be used not only in the correction phase, but also in the maintenance phase of the iron therapy of haemodialysis patients without causing toxicities. Hitherto, different amounts of iron have been administered, with initially higher dosages of iron ions being administered in the correction phase compared with the maintenance phase. Surprisingly, this different dosing is no longer required when using the combination preparations in accordance with the invention. The amount of the erythropoietin preparation and of the iron preparation are correlated optimally to each other in the combination preparation in accordance with the invention such that a differentiation between maintenance dose and correction dose is not required. Hereby, an increased safety in the treatment of patients is achieved, since the possibility of mistakes with respect to the optimal dosage of the individual preparations no longer exists.

In a further preferred embodiment the combination preparation contains as a further component a preparation which has a suppressive activity on TNF-alpha. Preferably, this is a gluco-corticosteroid, such as e.g. cortisone, a cortisol analogue or prednisolone derivative or an antimetabolite of folic acid, such as e.g. methotrexate. Preferred compounds are prednisone, prednilolone, 6 α-methyl-prednisolone, triamcinolone, paramethasone, dexamethasone, betmethasone, cortisone, cortisol and 16-methylene-prednisolone. The antiinflammatory activity of the EPO/iron dose is intensified synergistically.

When using the combination preparations, it is possible to administer the preparations, preferably the EPO preparation and the iron preparation, in a so-called fixed combination, i.e. in a single pharmaceutical formulation in which the compounds are present. This can comprise e.g. injection solutions, infusion solutions or lyophilizates, which, for example, are filled into ampoules. This administration form has the advantage that the EPO preparation is stabilized by the iron complex during the production and the storage of the administration form. The fixed combination of the active substances in the form of a lyophilizate has the further advantage of simple and safe handling. The lyophilizate is dissolved in the ampoule by the addition of pharmaceutically usual injection media and administered intravenously.

It is also possible to provide the preparations in the form of separate pharmaceutical formulations. As a rule, this is effected in the form of an individual unit pack which comprises several containers, with the first container being an administration form (lyophilizate, injection solution or infusion solution) containing the erythropoietin preparation and the second container being a suitable administration form for the iron preparation and optionally the third container being a suitable administration form of a TNF-alpha suppressor. The unit packs can also contain several individual dosage preparations of the respective preparations, so that, for example, a unit pack contains the requisite number of individual administration forms for a particular period (e.g. for weekly dosing).

This free combination, which can be made available in a single unit pack (medicament pack) also has the advantage that each patient to be treated can be prescribed a particular individual amount of an EPO preparation, of an iron preparation and optionally of a TNF-alpha suppressor. Furthermore, these combination preparations offer the advantage of greater safety when performing the therapy, since in each case the optimal synchronized amount of the individual preparation is fixed and a mistake with otherwise commercially available individual preparations, which are supplied in different dosages, can be largely excluded. Moreover, it has to be borne in mind that that in different countries medicinal preparations are often commercialized in different dosages for reasons of national requirements and there accordingly exists an increased danger of mistake with varying proportional amounts of the individual active substances. Further, the combination preparations in accordance with the invention minimize the risk of an inadvertently too high iron dose, which can possibly be given when conventional iron preparations from separate medicament packs are used together with the dose of an erythropoietin preparation. A safe therapy and simple handling by the personnel performing the treatment or in the area of self medication performed by patients is guaranteed by the combination preparation in accordance with the invention. In the present case it is e.g. also possible to provide one active substance as an injection solution and the other active substance (iron complex) as an administration form for oral administration.

Where the EPO preparation is made available as a lyophilizate, the medicament packs (combination packs) contain the corresponding amount of the EPO preparation in glass ampoules or in cartridges. The iron preparation can be present in solid form (tablet, powder, granulate, lyophilizate, etc) or also in liquid form in a separate container. Further, the combination pack preferably contains a reconstitution solution in order to dissolve either the active substance lyophilizate alone or also together with the solid iron preparation. If the iron preparation is present as a ready-for-use solution, the solution can be mixed together with the EPO solution when the combined administration of EPO and iron preparation has to be effected. Basically, the iron preparation can also be made available as a concentrate for addition to conventional infusion solutions, by which means a longer administration over several hours can be effected. In this case, a smaller volume of the iron complex-containing solution (about 0.5–10 ml) is added to the ready-for-use injection solution of about 500–1000 ml.

Combination preparations in the meaning of the present invention are also those unit packs which have a fixed optimal amount of the EPO preparation and of the iron preparation to be administered weekly. Advantageously, 5,000–50,000 U of an EPO preparation are administered weekly. This total dosage can be divided into several partial dosages for daily administration (i.e. 7 times per week) or for the administration of 1–6 partial amounts per week. The amount of the iron preparation to be administered weekly can be optionally divided into an amount corresponding to the weekly total dosage or also into several partial amounts for a repeated administration per week together with the erythropoietin preparation.

A further possibility in the meaning of the present invention comprises providing in each case individual administration forms of the erythropoietin preparation or of the iron preparation as an independent medicament, with the individual preparations being formulated such that they contain the requisite amounts of the individual substances for the combination in accordance with the invention of the EPO preparation and of the iron preparation. As a rule, the medicament packs contain the previously described package insert containing corresponding instructions for the combined administration with EPO or with iron preparations in the required amounts. A corresponding instruction can also be present as a pack imprint on the medicament pack (secondary packaging) or on the primary packaging (ampoule, blister strips, etc.). Thus, in the case of the EPO-containing medicament with 250–20,000 U of EPO it is, for example, indicated thereon that this preparation should especially be administered together with an iron complex preparation containing 1–40 mg, preferably 5–30 mg, of iron. In the case of the iron preparation there is a reverse indication to the combined administration with 250–20,000 U of an erythropoietin preparation.

A further possibility for providing the EPO preparations comprises making available corresponding multi-dose preparations which contain the EPO preparation in higher amounts compared with individual doses. These preparations are especially suitable for use in clinics in which a large number of patients are treated daily. These multi-dose preparations contain the EPO preparations in dosages of up to 500,000 U, especially up to 100,000 or 50,000 U. The multi-dose preparations have the advantage that they permit the skilled medical personnel to withdraw any dosage of the EPO preparation, for example by withdrawing corresponding amounts by volume of the finished injection solution. This is especially advantageous in the treatment of patients with different dosage requirements of the active substance or in the treatment of children in which a lower dosage of the EPO preparation is required. From an injection solution of, for example, 100,000 U of an EPO preparation, preferably freshly prepared at the beginning of the day, there can be performed, circumstances permitting, all patient treatments required during this day without the need to prepare separate injection solutions for each of the individual patients. This can lead to a significant time saving or to an easing of the burden of work for skilled medical personnel. Preferably, the individual EPO dosages are withdrawn in the range of 250 U, 500 U, 1,000 U and 10,000 U.

The multi-dose preparations can also be present in the form of solutions, which are filled into cartridges. These cartridges are suitable for use in so-called pens, which permit administration by patients themselves and an individual dosage withdrawal. For example, these cartridges contain the EPO preparation in an amount of 10,000 or 20,000 U, whereby dosing intervals of, for example, 250 U, 500 U, 1,000 U or 2,000 U are possible by appropriate adjustment of the withdrawal volume.

The production of the pharmaceutical administration forms is effected according to usual processes known in galenical technology using pharmaceutically usual adjuvants.

In connection with the diagnosis of rheumatic diseases and of iron metabolism disorders, especially the serum ferritin concentration can be determined in the meaning of the present invention. When a true iron deficiency occurs in addition to an already present rheumatic disease or anaemia, then the ferritin does not increase (it mainly remains below 90–95 ng/ml). In the case of simultaneous clinical symptoms of infection, inflammation or malignant disease this value points to a combination of iron deficiency and anaemia in conjunction with a rheumatic disease. Since the serum ferritin in these diseases can also react in the sense of an acute phase protein, the erythrocyte ferritin can be evaluated better diagnostically. The iron which is not required for erythropoiesis is stored by means of transferrin in two types of storage pools. The most important store is ferritin. This is a heterogeneous family of proteins which surrounds an iron nucleus. It is soluble and represents the active storage form in the liver (hepatocytes), bone marrow, spleen (macrophages), erythrocytes and in the serum (about 100–300 µg/l). The tissue ferritin pool is very labile and rapidly available when iron is required. The circulating serum ferritin originates from the reticuloendithelial system and its circulating concentration runs parallel with the total body iron (each ng/ml corresponds to 8 mg of iron reserve).

In performing the combination therapy with the combination preparation in accordance with the invention the weekly maximal dosage can be decided in a very simple manner by determining the diagnostic parameters for the iron status, especially the iron, transferrin, transferrin saturation, transferrin receptor and ferritin parameters. The patient is indicated to be optimally adjusted in the correction and maintenance phase when ferritin is: 100–300 µg/l (corresponding to stored iron(III) of 800–1200 mg) and the transferrin saturation is: 20–40%.

Preferably, the ferritin concentration is at least 100 µg/l, especially at least 150 µg/l, and a maximal up to 300 µg/l, especially a maximal up to 250 µg/l. The iron concentration is advantageously between 10–20 µmol/l (corresponding to about 56–112 µg/dl) and the transferrin concentration is between 30–60 µmol/l (corresponding to about 240–480 mg/dl). The transferrin saturation is defined as the ratio of serum/plasma iron concentration to serum/plasma transferrin concentration (multiplied by a correction factor of 1.41). It is thus a non-dimensional number which is independent of the hydration status of the patient. The transferrin saturation is calculated according to the formula Transferrin saturation (%)=(iron [mg/dl]×100)/(transferrin [mg/dl]×1.41)

An optimal adjustment of the patient is achieved when the ratio of transferrin saturation (in %) to the ferritin concentration (in µg/l) lies in the range of 5–40%. This parameter is defined as the transferrin/ferritin saturation (TfF saturation). It is calculated according to the formula TfF saturation=(transferrin saturation in %)×100/(ferritin [µg/l])

The value for this parameter preferably lies in the range of 10–40, especially at 15–25 [%×1/µg].

The optimal adjustment of the patient is checked diagnostically by means of this parameter, e.g. with the administration of 1 to 6 ampoules, preferably up to 3, 4 or 5 ampoules, in the week (one ampoule contains 500–7,500 U of rhEPO and 1–20 mg of iron complex).

In order to reliably exclude undesired side effects, the acute phase parameter CRP (5 mg/l±100%)[CRP=C-reactive protein] is measured, with the CRP at present being the best protein marker of an inflammatory reaction. Other parameters are TNF-alpha (Tumor Necrosis Factor alpha) and IL-6 (interleukin 6) or IL-1, IL-2 and IL-8. TNF-alpha should be <30 pg/ml (in plasma, ELISA) and IL-6 should be <20 pg/ml (in plasma, ELISA). In addition, the liver parameters GPT (glutamate pyruvate transaminase), GOT (glutamate oxalacetate transaminase) and γ-GT (gamma-glutamyl transferase) can be determined and should lie in the following ranges (determination at 37° C.): GPT:<50 U/l; GOT:<50 U/l;γ-GT:<40 U/l . In this connection, the GPT parameter currently stands in first position in liver diagnostics.

Furthermore, if desired, the haematological control parameters such as haematocrit (amount of red blood corpuscles in the total volume) or the increase in hypochromic erythrocytes can be relied upon. When the control parameters show a high increase, the weekly iron dose has to be reduced and then additional rhEPO should be administered. When the control parameters, primarily the transferrin saturation, show a lower value, the weekly iron dose has to be increased.

Furthermore, in the meaning of the present invention it has surprisingly been found that the establishment for patients of an individual optimal therapeutic dosage of EPO and of iron ions for the treatment of anaemia can be effected by determining the soluble TfR (transferrin receptor). The optimal therapeutic dosage of EPO and of iron(III) is obtained when the concentration of soluble TfR no longer increases. In order to insure that sufficient mobilizable iron is present, the i.v. iron dose and the EPO dose are increased in turn until a plateau has been reached. This corresponds to a concentration of 1,500–2,000 µg/l TfR.

In performing the combination therapy with the combination preparation in accordance with the invention for treatment of anaemia the weekly maximal dosage can be decided in a very simple manner by determining the diagnostic parameters transferrin receptor (TfR) and ferritin and the ratio of TfR to ferritin. The patient is indicated to be optimally adjusted in the correction and maintenance phase when ferritin is: 100–300 µg/l (corresponding to stored iron(III) of 400–1200 mg) and TfR/ferritin is: >15.

The TfR concentration is advantageously between 1,500–2,500 µg/l. The ratio of the concentrations TfR (in µg/l) to ferritin (in µg/l) lies especially in the range of 15–35, preferably at values above 20.

The optimal adjustment of the patient is checked diagnostically by means of this parameter, e.g. with the administration of 1 to 6 ampoules, preferably up to 3, 4 or 5 ampoules, in the week (one ampoule contains, for example, 3,000 U of rhEPO and 5 mg of iron complex. In this connection, these are not haemodialysis patients, but patients (e.g. rheuma patients) who, because of otherwise caused anaemia, are treated with EPO and/or iron preparations.

As already indicated, in order to reliably exclude undesired side effects, the acute phase parameter CRP (2–10 mg/l)[CRP=C-reactive protein] is measured; in addition the liver parameter GPT (glutamate pyruvate transaminase), which should be <50 U/l at 37° C. (<30 U/l at 25° C.) can be determined. Furthermore, if desired, the haematological control parameters such as haematocrit (amount of red blood corpuscles in the total volume) or the increase in hypochromic erythrocytes can be relied upon. In this connection, the reticulocytes can increase to a value of up to 15/1,000–30/1,000. The typical haemoglobin concentration lies at 12–18 g/dl. When the soluble TfR shows a high increase, the weekly iron dose has to be increased to up to 35 mg. When the soluble TfR shows lower values, the weekly EPO dose has to be increased.

The determination of the iron status is effected by the analysis of samples of body fluids (blood, serum, urine, etc.) of the patients in question. In order to determine the iron status, the concentration of iron, transferrin, ferritin and transferrin receptor, the transferrin saturation and the transferrin/ferritin saturation are determined in particular. In the case of haemodialysis patients, the parameters iron, transferrin, ferritin and transferrin saturation are preferably determined according to usual analytical methods. The determination of the transferrin/ferritin saturation value is especially relevant. In the case of anaemia patients whose anaemia is not caused by haemodialysis, the ferritin concentration and the concentration of the transferrin receptor are primarily determined. The determination of the ratio of transferrin receptor to ferritin (transferrin receptor/ferritin saturation value) is especially relevant.

In this sense, an optimal combination preparation in accordance with the invention for the treatment of patients with rheumatic diseases comprises 500–10,000 U, especially 2,000–4,000 U, of an EPO preparation and 3–10 mg, preferably 5 mg, of iron ions, preferably a Fe(III) complex, whereby the EPO preparation and the Fe(III) complex can be present in separate administration forms or in a single administration form. The administration forms in accordance with the invention also permit an administration of the iron preparation 1 to 3 days prior to the EPO preparation in order to top up the iron store prior to the beginning of the EPO treatment The concentration of iron in the blood and the iron binding capacity are determined in clinical chemistry in order to investigate iron metabolism. Both tests should always be carried out, since the relation of their measured results to each another is important Usually, the normal serum levels lie between 75 and 150 µg/dl in men and between 60 and 140 µg/dl in women. The total iron binding capacity is between 250 and 450 µg/dl. The serum iron level varies over the course of the day. It is lowered in the case of iron deficiency and in the case of anaemias associated with chronic illnesses. It is increased in the case of haemolysis and in the case of syndromes with iron over-loading (e.g. haemochromatosis or haemosiderosis). Patients under oral iron medication can have normal iron serum levels, although actually an iron deficiency is present in them. The total iron binding capacity (=transferrin×2) is increased in the case of iron deficiency; on the other hand it is lowered in the case of anaemias in the course of chronic illnesses.

Moreover, the serum ferritin level is determined. Ferritin is an iron-storing glycoprotein, of which tissue-typical isoferritins exist and which can be determined immunologically in serum, e.g. by a radioimmunoassay (RIA) or also by turbidimetric methods. The ferritin value is a measurement of the iron store in tissue. In most laboratories the normal range lies between 30 and 300 ng/ml and the geometric median value is 88 in men and 49 in women. The serum ferritin values stand in close relation to the total iron store of the body. Therefore, a lowered serum ferritin level is found only in the case of iron deficiency. An increased level is found in the case of iron over-loading. Likewise, an increased serum ferritin level is found in liver damage or in association with many neoplasms where ferritins can also be bonded to acute phase proteins. The serum transferrin receptor can also be determined by an enzyme-enhanced immunoabsorption test (enzyme-linked immunosorbent assay= ELISA). In this, a monoclonal antibody against the soluble receptor is used. The reference range lies between 0.5–3 mg/l. The level is increased in the case of a slight deficiency in the iron stores. The concentrations of specific erythrocyte ferritins can be determined in order to characterize the iron store, especially when the serum ferritin is not utilizable in the case of tissue damage or by acute phase reactions.

Further, the erythrocyte ferritin level is also determined in order to investigate the iron metabolism. The erythrocytes are separated from the leukocytes and thrombocytes (which likewise contain ferritin) in heparinized blood by centrifugation. Lysis of the erythrocytes and the immunological determination of the stored ferritin then follow. The erythrocyte ferritin reflects the status of the iron store during the preceding 3 months (i.e. during the lifetime of an erythrocyte). The normal values generally lie between 5 and 48 atom gram (ag) per erythrocyte. Values<5 are found in iron deficiency anaemias and elevated values (often >100) are found in the case of iron over-loading (e.g. haemochromatosis). The determination of zinc protoporphyrin has a similar affirmative validity.

The invention is illustrated hereinafter on the basis of an example which has been performed.

EXAMPLE 1

11 patients with visible rheumatoid arthritis and chronic inflammatory anaemia (Hb in the case of women <12 g/dl, in the case of men <13 g/dl) were treated over 12 weeks with 150 IU of EPO/kg body weight 2× weekly s.c. and additionally by i.v. administration of iron sucrose 200 mg/week on the appearance of a functional iron deficiency. A subsequent observation period took place over a further 12 weeks.

The course of therapy was investigated on the basis of the primary efficacy criteria (vitality scale SF-36, fatigue scale (MAF), isometric muscle strength (MSI)) and the secondary efficacy criteria, namely the disease activity parameters DAS (Disease Activity Score), RADAI (Rheumatoid Arthritis Disease Activity Index) as well as acute phase parameter CRP (C-reactive protein):

RESULTS

As will be evident from attached FIG. 1, the therapy proceeded positively. With respect to muscle strength, an average MSI increase of 8% was recorded, the vitality rose on average by 14% on the vitality scale SF-36 and the fatigue could be lowered by 8.3 out of 50 possible points.

Figure 2:
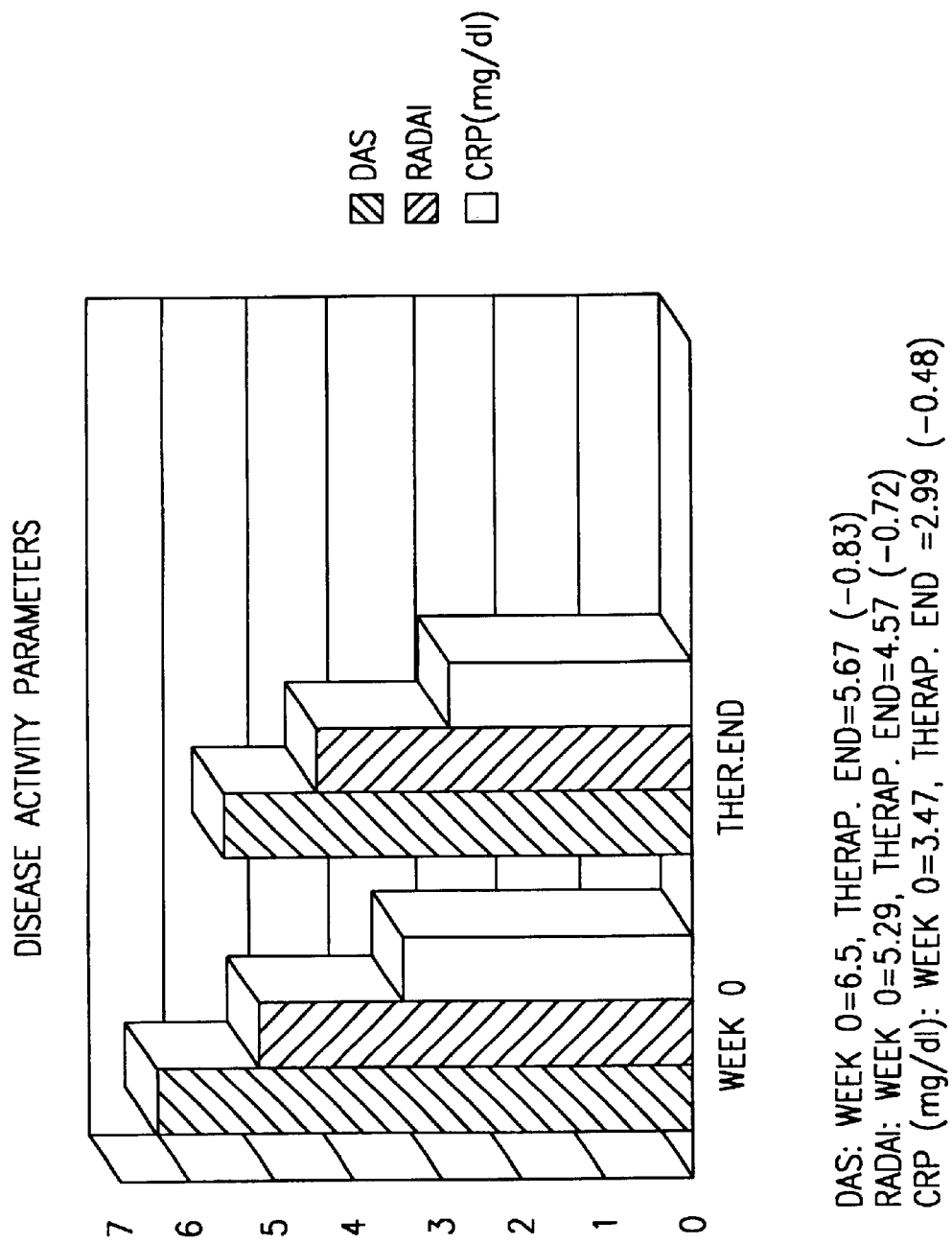
FIG. 2: Effects of treatment with EPO and iron sucrose according to Example 1. Disease Activity Score (DAS) Rheumatoid Arthritis Disease Activity Index (RADAI) and Acute Phase Parameter C-reactive protein (CRP) are shown.

The effects of the therapy on the disease activity parameters DAS, RADAI and CRP can be concluded from FIG. 2.

Thus, at the commencement of therapy the DAS had a value of 6.5, which lay at 5.67 at the end of therapy. The RADAI was 5.29 at the commencement of therapy and 4.57 at the end of therapy, and CRP (mg/dl) was 3.47 at the commencement of therapy and 2.99 at the end of therapy.

What is claimed is:

1. A method of treating the activity of a rheumatic disease in patients comprising administering to said patient suffering from said rheumatic disease a combination therapy comprising a first component consisting of 250 to 15,000 U of an erythropoietin preparation and a second component, consisting of an amount of a physiologically compatible iron preparation, which iron preparation administers to said patient from 1 to 40 mg of iron ions, each said components in said combined therapy being administered from 1 to 7 times weekly with the total amount of iron ions administered to said patient being no greater than 100 mg per week and administering said combination therapy for a period of time sufficient to reduce the activity of said disease.

2. The method of claim 1, wherein each erythropoietin administration contains from 500 to 10,000 U of erythropoietin.

3. The method of claim 1, wherein each iron preparation administration corresponds to an equivalent amount of from 1 to 30 mg of iron ions.

4. The method of claim 3, wherein each iron preparation administration corresponds to an equivalent amount of from 3 to 20 mg of iron ions.

5. The method of claim 1, wherein each erythropoietin administration contains from 250 to 20,000 U of erythropoietin and each iron preparation administration corresponds to an equivalent amount of from 1 to 30 mg of iron ions.

6. The method of claim 5, wherein each erythropoietin administration contains from 500 to 10,000 U of erythropoietin and each iron preparation administration corresponds to an equivalent amount of from 3 to 20 mg of iron ions.

7. The method of claim 1, wherein the iron preparation is a complex having a molecular weight from 30 kilodaltons to 100 kilodaltons.

8. The method of claim 7, wherein the iron preparation is Fe(III) saccharate.

9. The method of claim 7, wherein the iron preparation is Fe(III) gluconate.

10. The method of claim 1, where said iron preparation is administered to said patient in an amount to provide no more than 50 mg of iron ions per week.

11. The method of claim 1, wherein the rheumatic disease is an inflammatory joint disease.

* * * * *

UNITED STATES PATENT AND TRADEMARK OFFICE
CERTIFICATE OF CORRECTION

PATENT NO. : 6,372,715 B1
DATED : April 16, 2002
INVENTOR(S) : Joachim P. Kalteasser et al.

It is certified that error appears in the above-identified patent and that said Letters Patent is hereby corrected as shown below:

Column 11, line 41 - Column 12, line 30,
Replace claim 1 with:
1. A method of treating a patient suffering from rheumatic disease comprising administering to said patient a combination therapy comprising a first component consisting of 250 to 20,000 U of an erythropoietin preparation, and a second component, consisting of a physiologically compatible iron preparation, said iron preparation, consisting of from 1 to 40 mg of iron ions, wherein each of said components in said combined therapy is administered from 1 to 7 times weekly with the total amount of iron ions administered to said patient being no greater than 100 mg per week and administering said combination therapy for a period of time sufficient to reduce the severity of disease.

Signed and Sealed this

First Day of July, 2003

JAMES E. ROGAN
*Director of the United States Patent and Trademark Office*